United States Patent [19]
Russell et al.

[11] Patent Number: 5,443,464
[45] Date of Patent: Aug. 22, 1995

[54] EXTERNAL FIXATOR APPARATUS

[75] Inventors: Thomas A. Russell, Memphis, Tenn.; Harry E. Lee, Jr., Southhaven, Miss.

[73] Assignee: Memphis Orthopaedic Design, Inc., Memphis, Tenn.

[21] Appl. No.: 17,933

[22] Filed: Feb. 16, 1993

[51] Int. Cl.⁶ .............................................. A61B 17/60
[52] U.S. Cl. ........................................ 606/54; 606/56; 606/59
[58] Field of Search .................. 606/53, 54, 55, 56, 606/57, 58, 59, 73, 72; 403/365, 366, 367

[56] References Cited

U.S. PATENT DOCUMENTS

| | | |
|---|---|---|
| 3,171,408 | 3/1965 | Childs et al. . |
| 4,135,505 | 1/1979 | Day . |
| 4,235,428 | 11/1980 | Davis . |
| 4,273,116 | 6/1981 | Chiquet . |
| 4,299,212 | 11/1981 | Goudfrooy . |
| 4,615,338 | 10/1986 | Ilizarov et al. . |
| 4,620,533 | 11/1986 | Mears . |
| 4,662,365 | 5/1987 | Gotzen et al. ............. 606/54 |
| 4,693,240 | 9/1987 | Evans . |
| 4,739,751 | 4/1988 | Sapega et al. . |
| 4,889,111 | 12/1989 | Ben-Dov ................... 606/54 |
| 4,895,141 | 1/1990 | Koeneman et al. . |
| 4,923,458 | 5/1990 | Fischer ...................... 606/59 |
| 4,946,458 | 8/1990 | Harms et al. . |
| 5,003,969 | 4/1991 | Azer et al. . |

FOREIGN PATENT DOCUMENTS

| | | |
|---|---|---|
| 2499400 | 8/1982 | France . |
| 2101488 | 1/1983 | United Kingdom ........... 606/72 |
| 0480579 | 4/1992 | United Kingdom . |
| 0481664 | 4/1992 | United Kingdom . |
| 0481697 | 4/1992 | United Kingdom . |
| 0490812 | 6/1992 | United Kingdom . |

Primary Examiner—Tamara L. Graysay
Attorney, Agent, or Firm—Baker, Donelson, Bearman & Caldwell

[57] ABSTRACT

An external fixation system for stabilizing bone fractures is provided, having a hexagonal rod as the primary support mechanism with a plurality of fixation components adjustably secured thereto. The fixation components preferably include at least one pin secured to the hexagonal rod by a clamping mechanism which provides multiple degrees of adjustability for enhanced pin placement. The clamping mechanism comprises a clamp member and ball collet having a hexagonal opening formed therein, wherein the ball collet fits within a cavity in the clamp member with the rod extending therethrough, and a retaining nut used to compress the ball collet thereby grippingly engaging the rod and securing the clamp member to the rod. The clamp member is adjustable to any desired position both longitudinally and peripherally about the rod. Each pin is secured within a clamp member through the use of similar ball collets and retaining nuts, and is angularly adjustable relative to the clamp member. In the preferred embodiment, a ring member may also be attached to the rod, with additional fixation components such as tension wires, buttress pins, and the like, adjustably secured to the ring member by similar clamping mechanisms.

11 Claims, 6 Drawing Sheets

EXTERNAL FIXATOR APPARATUS

BACKGROUND OF THE INVENTION

1. Field

This invention relates to an apparatus for the external fixation and stabilization of a fractured bone and, more particularly, to such apparatus having enhanced adjustability for precise pin placement.

2. Description of the Prior Art

External fixation devices have been utilized for a number of years for setting and stabilizing fractured bones. While fixator devices and systems have undergone considerable evolutionary changes over the years, they all consist essentially of means for rigidly holding the sections of a broken bone in alignment throughout the healing process. Such apparatus may comprise a relatively crude splint or cast, or may comprise a more modern and sophisticated system involving surgical pins secured to an external fixator bar, or the Ilizarov system well known to those skilled in the art.

A common fixator systems currently on the market comprises a hexagonal fixator bar used to interconnect and rigidly secure a plurality of surgical pins inserted into the fractured bone at various points, with each surgical pin being retained within a clamp secured to the hexagonal bar. Each clamp is installed onto the hexagonal bar by sliding the clamp over one end or the other and tightening one or more nuts when the clamp is in its desired longitudinal position on the bar. Each clamp holds at least one pin at a fixed angle relative to the clamp, with all pin movement at any given longitudinal clamp location being constrained within a plane at rights angles to the bar. When pin clamps having multiple pins are employed, all pins within a single clamp are confined to the same alignment without any freedom for independent placement.

A number of significant problems with the above described fixator system have become evident to those skilled in the art. Placement of the surgical pins in a fractured bone is always a concern to the surgeon and, in some cases, may be of critical importance. With the above described system, optimal adjustment of a clamp for precise pin placement can be extremely difficult and time consuming, under circumstances where time is at a premium. In certain situations, optimal placement of all pins is impossible due to the nominal adjustment capabilities of the pins relative to the clamps.

Several efforts have been made to improve the adjustability of external fixators, including the devices shown in French Patent No. 2,499,400, issued Aug. 13, 1982 to Tornier, European Patent Application No. 490,812, published Jun. 17, 1992 to Mata, et al., U.S. Pat. Nos. 4,273,116, issued Jun. 16, 1981 to Chiquet, 4,620,533, issued Nov. 4, 1986 to Mears, 4,895,141, issued Jan. 23, 1990 to Koeneman, et al., 4,693,240, issued Sep. 15, 1987 to Evans, and 4,299,212, issued Nov. 10, 1981 to Goudfrooy. The inventions shown in each of these references have proven to be either too cumbersome to use and/or insufficiently effective to warrant the additional cost and trouble.

In light of the above described prior art and problems associated therewith, a significant need has arisen for a relatively simple external fixator having multiple degrees of adjustability that is easy to use and provides a wide range of pin orientations and positions.

BRIEF SUMMARY OF THE INVENTION

A primary object of the present invention is to correct the above noted deficiencies in the prior art. In particular, this invention comprises an external fixation system having a degree of pin placement selection previously unknown in the art.

Another object of this invention is to provide a high degree of adjustability in an external fixation system in a manner that facilitates assembly of the fixator apparatus. A further object is to facilitate and minimize the time required to adjust the position of the surgical pins.

A still further object of this invention is to provide an apparatus which allows for optimal placement of each of a plurality of surgical pins in an external fixator system.

Another object is to provide a system for attaching pins or other components to a fixator bar which is simple to assemble and adjust, and provides a wide range of adjustment.

To achieve these and other objects, the present invention comprises a hexagonal fixator bar having a plurality of pins removably securable thereto through a unique mounting bracket assembly. Each mounting bracket is secured to the hexagonal bar by a specially adapted ball collet and retaining nut, wherein the bracket is freely moveable both longitudinally and rotationally upon loosening a single retaining nut, and fixed in place upon tightening thereof. The ball collet has a hexagonal opening for grippingly engaging the hexagonal bar upon compression caused by tightening the retainer nut. The hexagonal opening greatly improves the resistance to rotation about the fixator bar. Each surgical pin is retained within a bracket via a similar ball collet and retainer nut assembly, with each pin being adjustable up to thirty (30°) degrees in any direction relative to the bracket. The rigidity of this system is improved by forming all components from titanium, thereby enhancing the engagement of the ball collets with the brackets, pins, and hexagonal bar, and reducing the likelihood of inadvertent loosening of the retainer nuts and other components.

The above stated and other objects of this invention will become apparent to those skilled in the art upon reading the following detailed description, taken in conjunction with the enclosed drawings.

DETAILED DESCRIPTION OF THE PREFERRED EMBODIMENT

Figure 1:
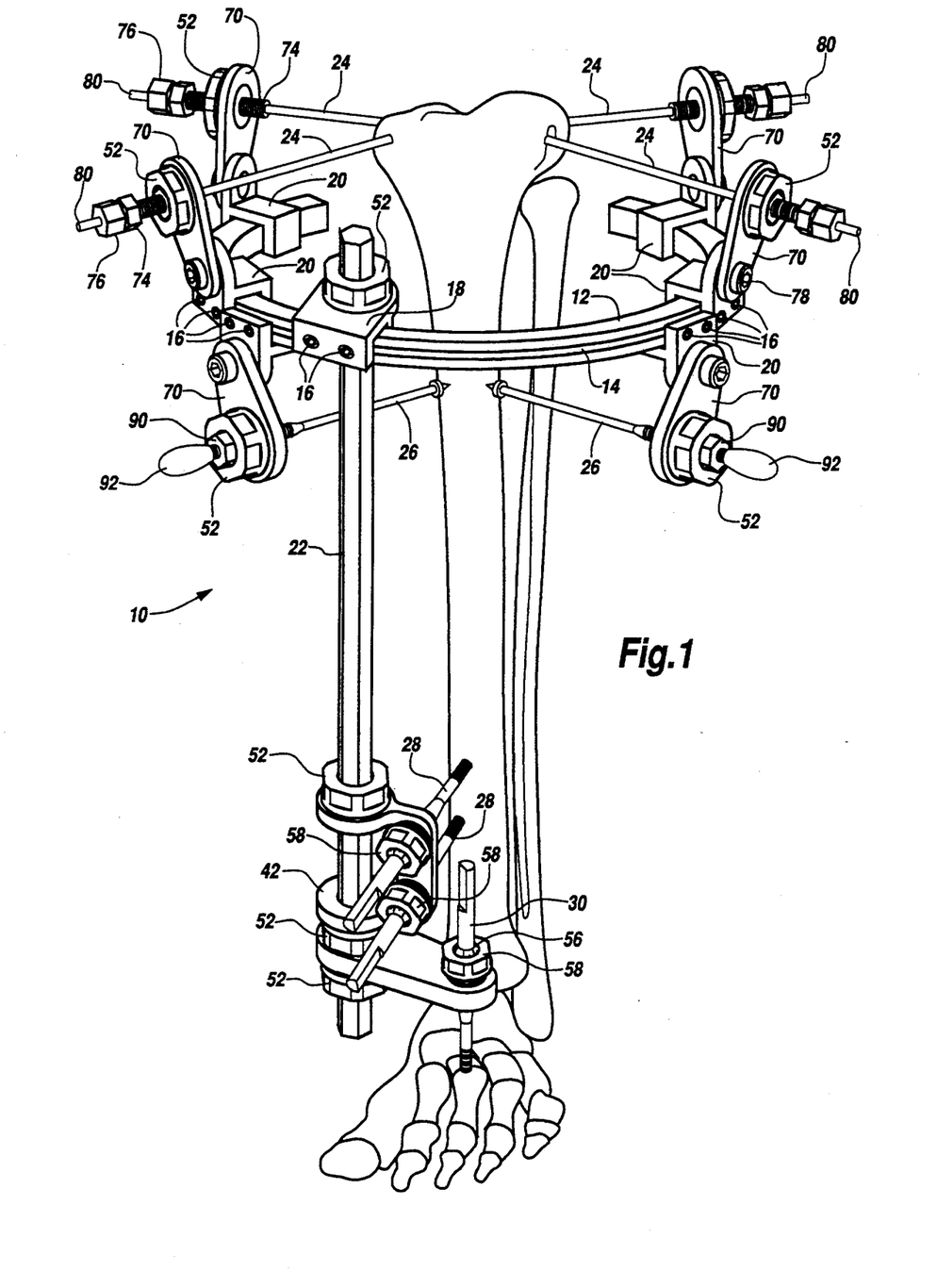
FIG. 1 is a front perspective view of an external fixation apparatus embodying the principals of the present invention.

The external fixation apparatus shown in FIG. 1 exemplifies one of a wide variety of assemblies made possible and simplified by the present invention. In this embodiment, external fixator 10 comprises a ring member 12 having generally planar parallel top and bottom surfaces and curved inner and outer surfaces. Ring member 12 serves as the foundation for mounting a variety of fixation components, with a V-shaped grove 14 formed in the outer surface of ring member 12 for engaging set screws 16 operatively disposed in clamps 18 and 20. As those skilled in the art will readily appreciate, clamp 18 comprises a ring-to-bar clamp for anchoring ring 12 to hexagonal bar 22, while clamps 20 are employed to anchor additional fixation components discussed more fully below. All such clamps 18 and 20 may be freely moved about ring member 12 upon loosening set screws at 16, and secured in the desired position by tightening set screws 16.

Fixator 10 shown in FIG. 1 includes a variety of components which may or may not be necessary for a given situation. Apparatus 10 comprises what may be generally referred to as a hybrid construct, utilizing a partial ring (ring member 12) wires 24, buttress pins 26, and fixation pins 28. Metatarsal pin 30 is also utilized on fixator 10, but may be omitted for other applications.

Figure 3:
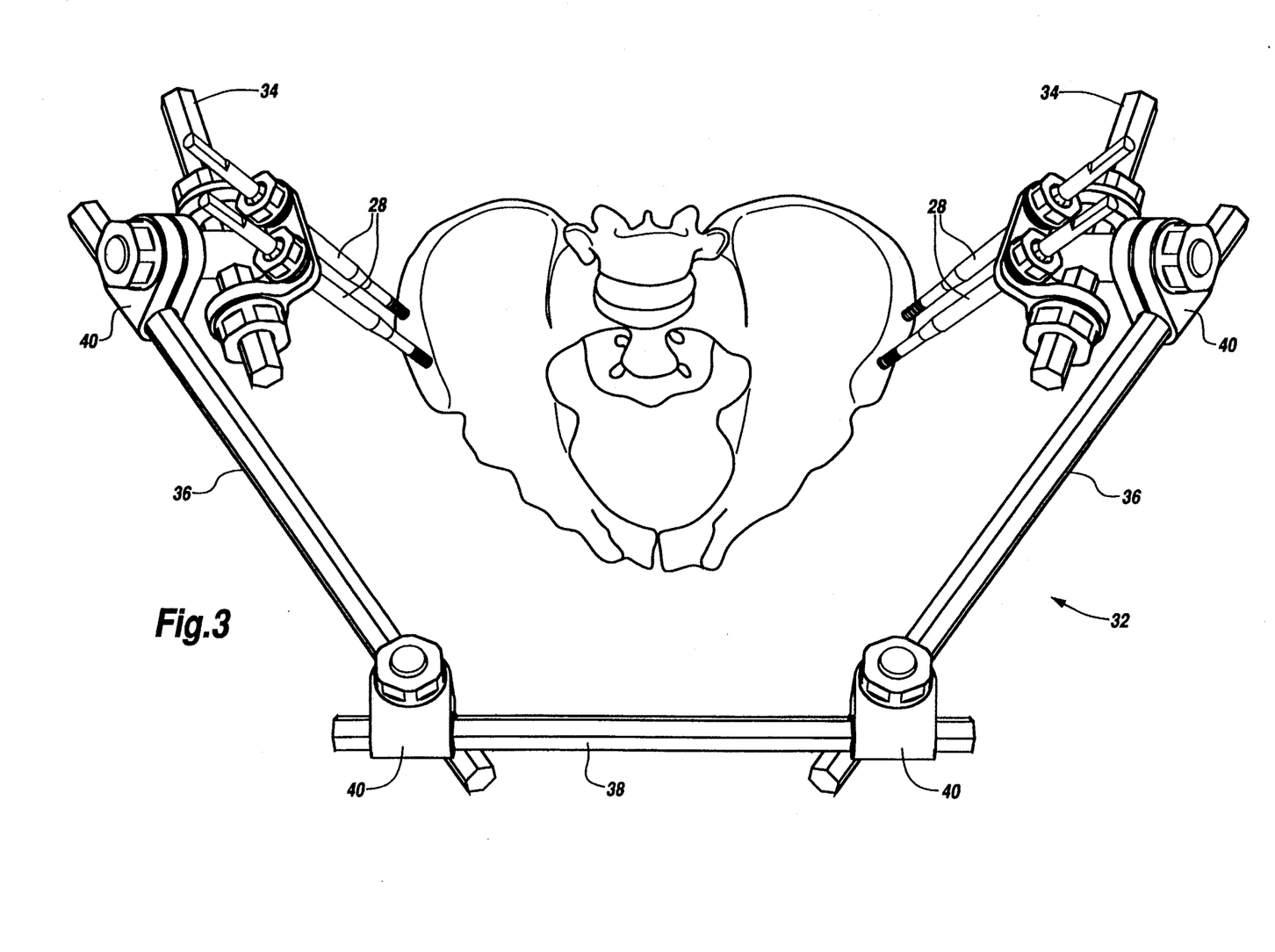
FIG. 3 is a perspective view of an external fixator embodying the principals of this invention specially adapted for use on a broken pelvis.

FIG. 3 illustrates an example of a pelvic fixator 32 embodying the principals of the present invention. This embodiment utilizes fixation pins 28 maintained in their proper position by a series of hexagonal bars 34, 36 and 38, which are interconnected by a plurality of clamps 40. As evidenced by the fixator systems shown FIGS. 1 and 3, it is to be understood that the unique properties of the present invention, discussed more fully below, are not specially limited to any particular fixation system or apparatus, but have widespread application for external fixators of the general nature disclosed herein.

Figure 1A:
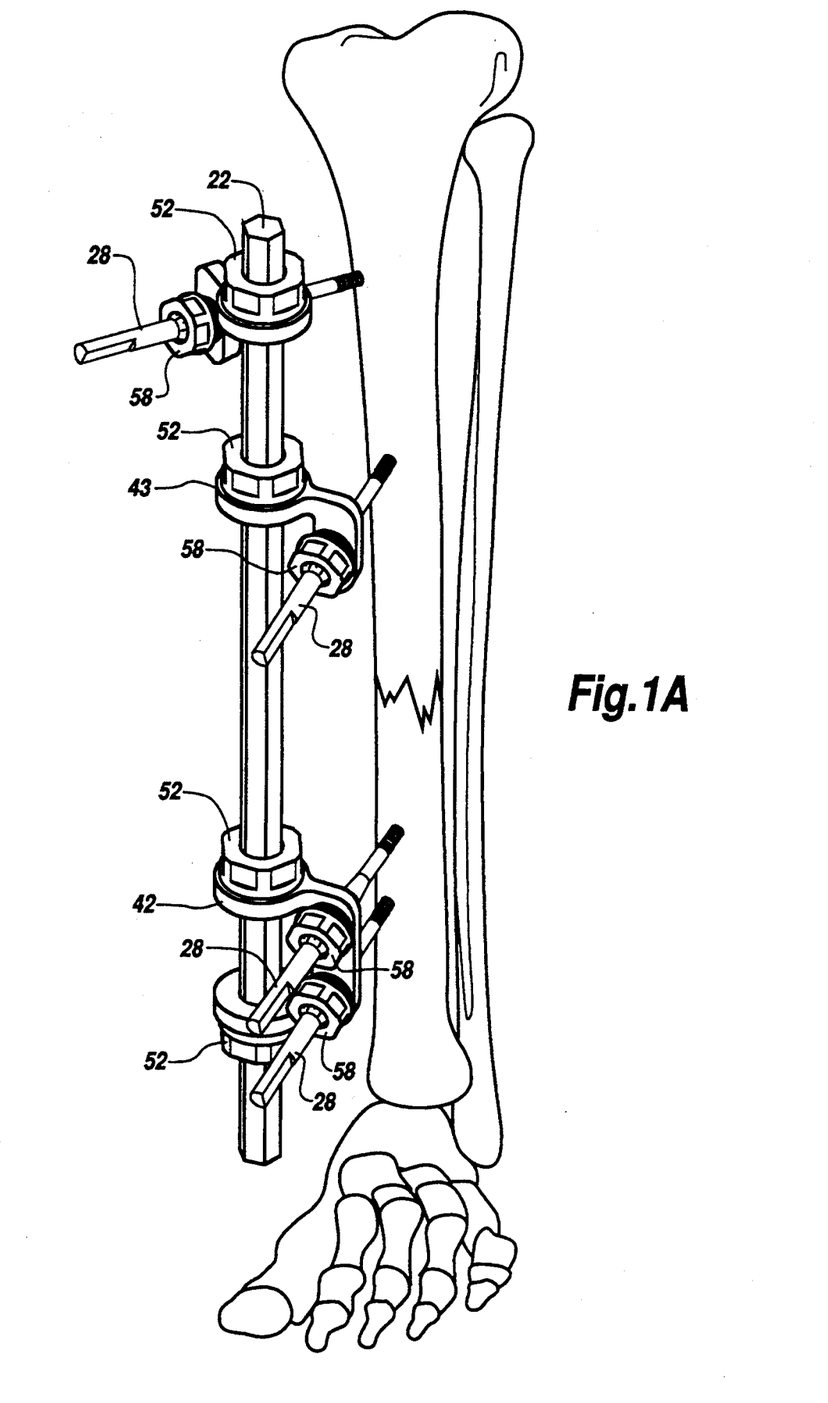
FIG. 1A is a perspective view of a single pin clamp used in an alternative embodiment of the invention.
Figure 2:
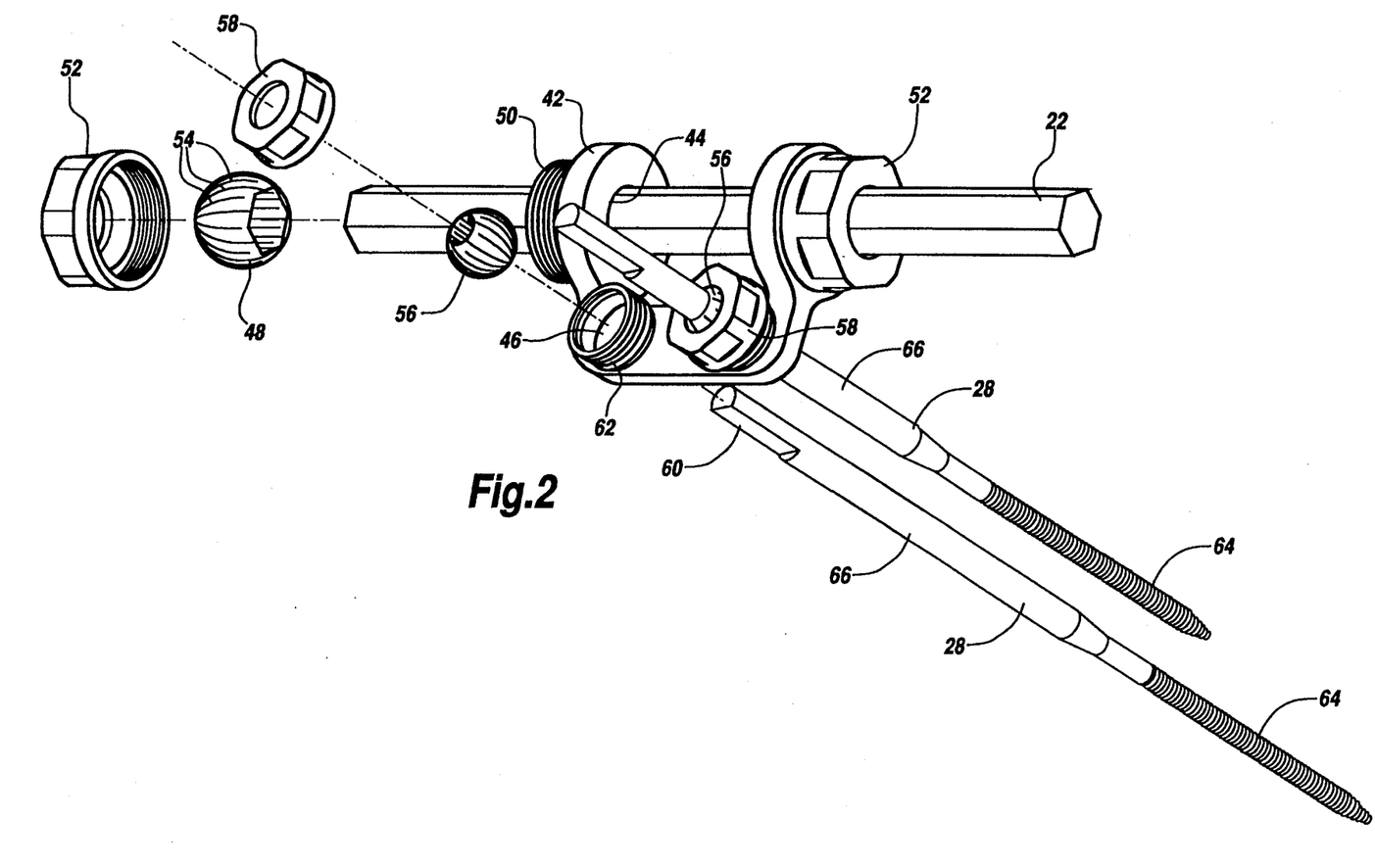
FIG. 2 is a partially exploded perspective view of a bracket assembly used for securing surgical pins to a hexagonal fixator bar.

Referring now to FIG. 2, a representative section of hexagonal bar 22 is shown having a pair of fixation pins 28 adjustably secured thereto through the unique clamping apparatus of the present invention. In the embodiment shown, clamp 42 is adapted to retain two fixator pins 28, with the body of clamp 42 having two generally circular holes 44 formed therethrough for receiving hexagonal bar 22, and a pair of holes 46 oriented at right angles thereto for receiving fixation pins 28. It is expected that clamp 42 may be adapted to retain any number of fixation pins 28 and, in particular, it will be common for clamp 42 to support only one fixation pin 28. In the single pin embodiment shown in FIG. 1A, the body of clamp 43 will have only one hole 44 and one hole 46, and essentially comprises half of clamp 42 described herein. To those skilled in the art, the structure of a single pin clamp will become apparent upon reviewing this specification.

Holes 44 are of sufficient diameter so that bracket 42 may be easily installed on either end of hexagonal bar 22 and moved longitudinally and rotationally as necessary to achieve the desired position. Ball collet 48, having a hexagonal opening formed therethrough only slightly larger than hexagonal bar 22, is then slid into place and seated within a suitable cavity formed in shoulder 50. With clamp 42 positioned as desired, retaining nut 52 may then be threaded on to shoulder 50. Tightening retaining nut 52 compresses ball collet 48 into the seat provided by the interior cavity of shoulder 50, thereby effectively locking clamp 42 into place on hexagonal bar 22. Ball collet 48 has a plurality of longitudinal slots 54 formed therein, which cooperate to enable the hexagonal opening through ball collet 48 to compress uniformly about the external surface of hexagonal bar 22. The novel use of a hexagonal opening in a ball collet 48, combined with the structure of clamp 42, provides a connection between hexagonal bar 22 and clamp 42 which is highly resistent to slippage, almost infinitely positionable, and simple to install and adjust. Upon loosening retaining nuts 52, clamp 42 may be moved longitudinally or rotated about hexagonal bar 22 to any desired position. Once the appropriate position has been achieved, retightening nuts 52 locks clamp 42 into place. With the single pin design, it will be understood that only one ball collet 48 and nut 52 need be employed.

Fixation pins 28 are retained within holes 46 in a similar manner utilizing ball collets 56 and retaining nuts 58. With ball collet 56 and retaining nut 58 loosely disposed on the non-threaded end 60 of a fixation pin 28, the fixation pin 28 is easily insertable into the fractured bone. Once fixation pin 28 is properly installed, retaining nut 58 is threaded onto shoulder 62 and tightened in place. Ball collet 56, being slotted in a similar manner to ball collet 48 described above, grippingly engages the shank portion 66 of fixation pin 28 and fixedly secures fixation pin 28 to clamp 42.

The use of ball collet 56 to secure fixation pin 28 within clamp 42 provides several distinct advantages for the present invention. Typically, a surgeon will require a wide range of fixation pins 28 having different sized threaded portions 64. With most conventional systems, the shank portion 66 of fixation pin 28 has approximately the same outside diameter as threaded portion 64. With the unique fixation pins 28 of this invention, however, shank portion 66 has a standard diameter regardless of the size of threaded portion 64. By standardizing the diameter of shank 66 for a plurality of different fixation pins 28, a single ball collet 56 may be utilized in every situation. This greatly reduces the number of components to be maintained and significantly simplifies assembly by the surgeon.

Figure 7:
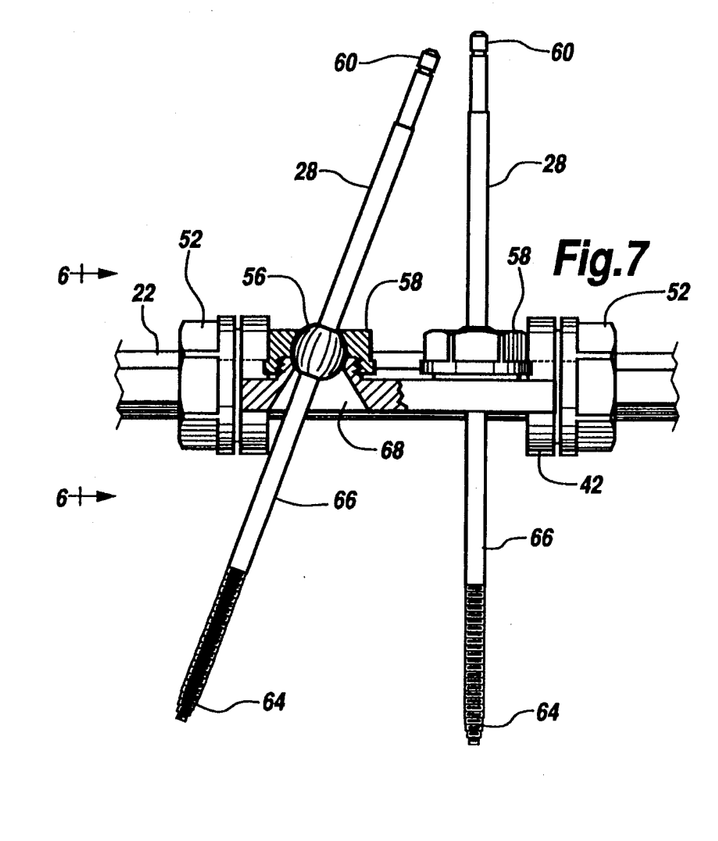
FIG. 7 is a front elevational view of the clamp assembly shown in FIG. 2, showing a surgical pin oriented at an angle.
Figure 8:
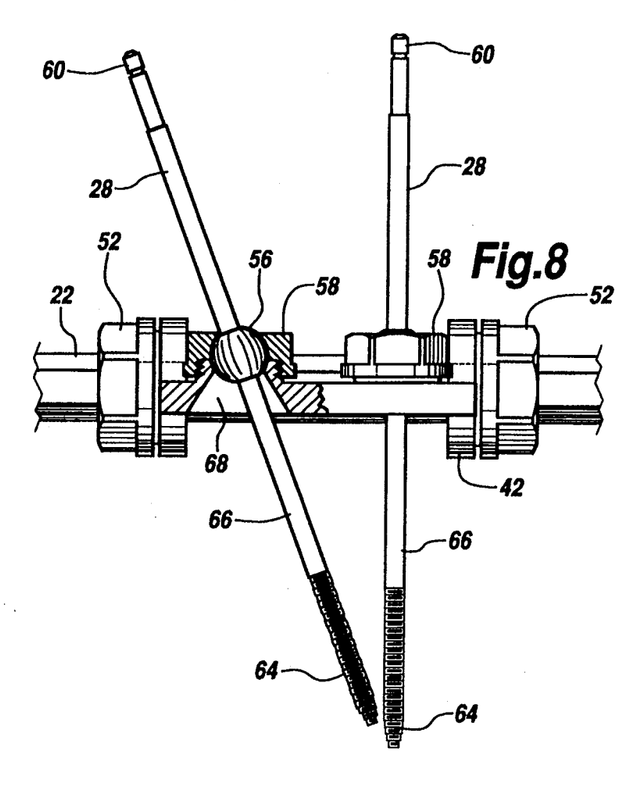
FIG. 8 is a front perspective view of the assembly shown in FIG. 7, showing the pin oriented in an alternative position.

A further advantage provided by this invention is the unusually high degree of adjustability allowed for the accurate placement of fixation pin 28. A shown in FIGS. 7 and 8, the underside of clamp 42 adjacent hole 46 has a conical area 68 formed therein, which allows substantial angular adjustability of fixation pin 28. In the preferred embodiment shown, fixation pins 28 may be moved through an angle of approximately thirty (30°) degrees from the center position in any direction. Furthermore, in a double pin clamp 42 as shown, each pin may be angularly adjusted completely independent of the other pin. If the surgeon desires even greater flexibility in the placement of two adjacent pins, a pair of single pin brackets may be utilized in place of the double pin clamp 42 shown herein. The present invention significantly reduces the restrictions on pin placement which present serious limitations on the overall performance of conventional fixation systems.

Figure 4:
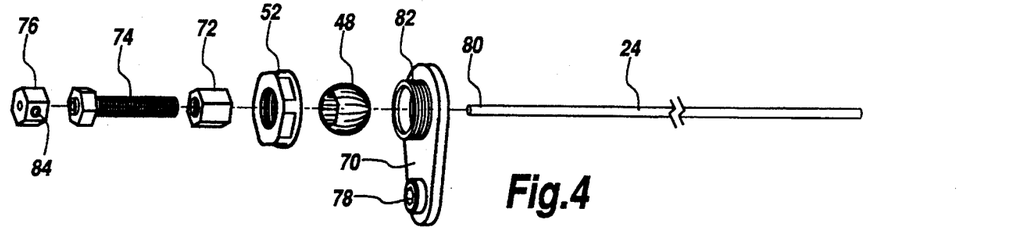
FIG. 4 is an exploded perspective view of the tension wire retention assembly according to the present invention.
Figure 5:
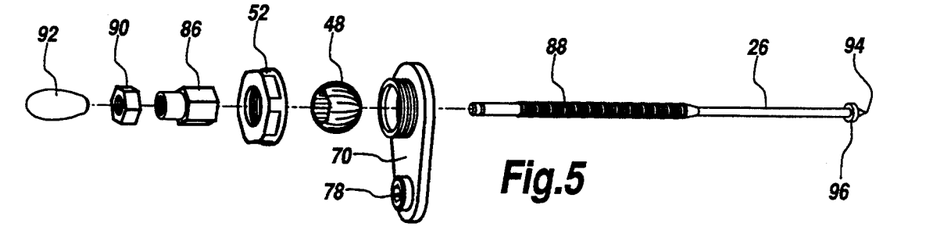
FIG. 5 is an exploded perspective view of a buttressing pin retention assembly according to the present invention.
Figure 6:
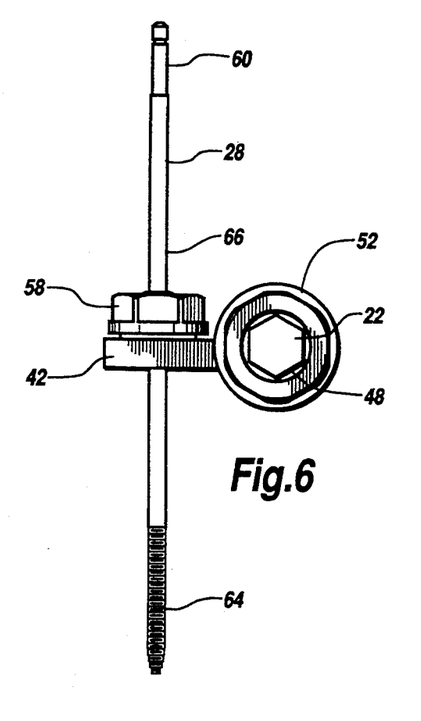
FIG. 6 is an end elevational view of a clamp assembly, taken along line 6—6 of FIG. 7.

Additional features of fixator 10 are illustrated in detail in FIGS. 4 and 5. Referring initially to FIG. 4, the retention assembly for a representative wire 24 is shown, comprising a bracket 70, a ball collet 48, a retaining nut 52, hexagonal member 72, threaded adjustment member 74, and end cap 76. As shown in FIG. 1, bracket 70 is adjustably securable to a clamp 20, preferably by means of a screw 78. After insertion of wire 24 through the end of a fractured bone as shown in FIG. 1, bracket 70 and the remaining components may be installed in place over each end 80 of wire 24. Hexagonal member 72 fits within the hexagonal opening in ball collet 48 and is secured therein upon tightening retainer nut 52 onto threaded shoulder 82, in much the same manner as discussed above regarding the anchoring of clamp 42 onto hexagonal bar 22. Adjustment member 74 threadingly engages the internal threaded opening of hexagonal member 72, with wire 24 being disposed through the longitudinal opening through adjustment member 74. With end caps 76 affixed to each end 80 by set screws 84, adjustment members 74 at opposite ends of wires 24 may be selectively rotated to produce the desired tension in wires 24 as needed under the circumstances.

In FIG. 5 the retaining assembly for a representative buttress pin 26 is disclosed, also comprising a bracket 70, ball collet 48, and retaining nut 52, which are operatively assembled in a manner generally similar to that described above. For use with buttress pin 26, however, hexagonal member 86 has an internal threaded opening adapted to engage the threaded portion 88 of buttress pin 26, with lock nut 90 being tightened thereon to prevent inadvertent loosening of buttress pin 26. It is to be understood that hexagonal member 86 is secured within the opening in ball collet 48 in the same manner as hexagonal member 72 and hexagonal bar 22 described above. Protective cap 92 is also shown in connection with buttress pin 26, but it is to be understood that a similar protective cap may also be used with fixation pins 28 and metatarsal pin 30 as desired.

Those skilled in the art will appreciate the fact that buttress pins 26 are designed to be substantially less intrusive than fixation pins 28, having a point 94 and shoulder 96 at the distal end thereof rather than a threaded portion 64. Point 94 is designed to penetrate only slightly into the exterior surface of the fractured bone, without penetrating the interior cavity as with conventional surgical pins. As such, buttress pins 26 are particularly well suited for use in areas involving a heightened risk of infection where it is advantageous to avoid drilling into the interior bone cavity. Additionally, since buttress pins 26 do not require a pre-drilled hole as do conventional surgical pins, they may be installed in less time and are therefore well suited for situations where a bone must be set quickly so that other injuries may be addressed.

It will be appreciated that the use of ball collet 56 and retaining nuts 52 in the retention assemblies for wires 24 and buttress pins 26 as described herein provides enhanced angular adjustability for these components heretofore unknown in the art. Furthermore, the use of standardized components in a variety of different applications greatly reduces the number of individual components which must be maintained for use by the surgical team. Standardized components used in this manner also increase the efficiencies of the surgical team by reducing the likelihood that the wrong component will be provided to the surgeon during critical portions of the procedure.

In the embodiment disclosed herein, all components (except protective cap 92) are preferably formed from titanium. The use of titanium for ball collets 48 and 56, retaining nuts 52 and 58, clamp 42, and hexagonal bar 22 insures slip-resistant engagement between these components due to the inherent galling tendency of titanium. An additional advantage is obtained by the non-magnetic properties of titanium, making the entire fixator 10 completely compatible with magnetic resonance imaging equipment.

While the basic principals of an improved external fixator having a degree of adjustability previously unknown in the art have been made clear from this detailed disclosure, it is to be expected that considerable variations may be made in the embodiments disclosed herein without departing from the spirit and scope of this invention. Accordingly, the significant improvements offered by this invention are to be limited only by the scope of the following claims.

What is claimed is:

1. An apparatus for external fixation and stabilization of a bone fracture, having:
   a plurality of pins insertable into the bone at discrete longitudinal positions, at least two said pins being insertable on opposite sides of the fracture, said pins having distal ends extendable laterally from said bone;
   a bar having a non-circular cross sectional configuration, disposed adjacent said distal ends of said pins and securable to said pins at an orientation generally parallel to said bone; and
   first and second clamping means for anchoring said pins to said bar to prevent relative movement therebetween, each said clamping means comprising:
      a clamp removably securable to said bar for interconnecting said bar and at least one of said pins, said clamp having a body with a pair of substantially perpendicular holes formed therethrough, the first said hole being adapted to allow said bar to pass therethrough and rotate freely therein, and the second said hole being adapted to allow said distal end of one of said pins to pass therethrough and rotate freely therein;
      first and second annular shoulders formed in said body adjacent said first and second holes, respectively, each said shoulder having an interior surface forming a seat;
      a first ball collet having an aperture formed therethrough, said aperture being adapted to slidably receive said bar and grippingly engage said bar upon compression of said ball collet, said aperture having a non-circular cross sectional configuration conforming to the cross sectional configuration of said bar whereby rotational movement of said ball collet about said bar is prohibited, said ball collet being seatable within said seat formed in said first shoulder; and
      a first nut, having a central opening formed therein for allowing said bar to pass therethrough, said nut being adapted to engage said shoulder formed adjacent said first hole thereby retaining and compressing said ball collet within said seat, whereupon
      loosening said first nut allows free rotation of said clamp about said bar, and tightening said nut causes said ball collet to grippingly engage said bar such that said clamp is fixed with respect to said bar.

2. An apparatus as set forth in claim 1, wherein each said clamping means further comprises:
   a second ball collet having an aperture formed therethrough, said aperture being adapted to slidably receive one of said pins and grippingly engage said pin upon compression of said second ball collet, said second ball collet being seatable within said seat formed in said second shoulder; and
   a second nut, having a central opening formed therein for allowing one of said pins to pass therethrough, said second nut being adapted to engage said shoulder adjacent said second hole thereby retaining and compressing said ball collet within said seat formed therein, whereupon
   loosening said second nut allows rotation and longitudinal movement of said pin while disposed through said aperture in said second ball collet, and tightening said second nut causes said second ball collet to grippingly engage said pin such that said clamp and said bar are fixed with respect to said pin.

3. An apparatus as set forth in claim 2, wherein:
   in each said first and second clamping means said second ball collet is rotatable within said seat upon loosening said second nut, thereby allowing selective angular adjustment of said pin relative to said clamp and said bar.

4. An apparatus as set forth in claim 3, wherein:
   said first and second shoulders have external threads formed thereon, and said first and second nuts have internal threads formed therein, said nuts being threadingly engageable with said shoulders.

5. An apparatus as set forth in claim 2, wherein:
   said bar and each said clamping means are formed from titanium.

6. An apparatus as set forth in claim 1, wherein:
   said bar has a hexagonal cross-sectional configuration.

7. An apparatus as set forth in claim 1, further comprising:
   a ring member adjustably secured to one end of said rod, said ring member at least partially encircling a portion of said bone;
   a plurality of buttress pins adjustably secured to said ring member, each said buttress pin having a proximate end secured to said ring member and a distal end bearing on said bone, said distal end being adapted to engage the outer surface of said bone without penetrating the central cavity thereof.

8. An apparatus as set forth in claim 1, wherein:
   at least one of said clamps includes a third hole for retaining a third pin.

9. An apparatus as set forth in claim 1, wherein:
   at least one of said clamps includes a third hole aligned with said first hole and adapted for securing said clamp to said bar, said first hole and said third hole being longitudinally spaced apart along said bar upon assembly of said apparatus.

10. An apparatus for external fixation and stabilization of a bone fracture, comprising:
    a hexagonal fixator bar securable generally parallel to said bone in the vicinity of said fracture;
    a plurality of clamps spaced longitudinally along said bar and secured thereto; and
    a plurality of fixation pins operatively secured to said clamps and extending generally laterally relative to said bar, each said pin having a proximate end secured to one of said clamps and a distal end engageable with a portion of said bone, wherein;
    each said clamp is selectively anchored to said bar by a first ball collet having a hexagonal opening formed therethrough and being adapted to fit within a first cavity formed in said clamp with said bar passing longitudinally through said opening, said first ball collet being compressible to grip said first cavity and said bar, and a first retaining nut selectively engageable with said clamp which, upon tightening thereof, operatively compresses said first ball collet thereby fixing said clamp relative to said bar, whereupon loosening said first retaining nut allows longitudinal and rotational movement of said clamp relative to said bar.

11. An apparatus as set forth in claim 10, wherein:
    each said clamp is adapted to retain at least one said fixation pin by retaining means comprising:
    a second ball collet having an opening formed therethrough and being adapted to fit within a second cavity formed in said clamp with said pin passing longitudinally through said opening, said second ball collet being compressible to engage both said second cavity and said pin; and
    a second retaining nut selectively engageable with said clamp which, upon tightening thereof, compresses said second ball collet thereby fixing said pin relative to said clamp, whereupon loosening of said second retaining nut allows longitudinal and angular movement of said pin relative to said clamp.

* * * * *